United States Patent

Scherson et al.

Patent Number: 5,855,570
Date of Patent: *Jan. 5, 1999

[54] OXYGEN PRODUCING BANDAGE

[76] Inventors: Daniel A. Scherson, 2568 Saybrook Rd., University Hts., Ohio 44118; Melvyn I. Burk, 21001 Halburton Rd., Beachwood, Ohio 44122

[*] Notice: The term of this patent shall not extend beyond the expiration date of Pat. No. 5,578,022.

[21] Appl. No.: 753,421

[22] Filed: Nov. 25, 1996

Related U.S. Application Data

[63] Continuation of Ser. No. 421,679, Apr. 12, 1995, Pat. No. 5,578,022.
[51] Int. Cl.$^6$ .................................................. A61F 13/00
[52] U.S. Cl. ................................ 604/304; 607/50
[58] Field of Search ................ 604/20, 303, 304, 604/305, 306, 307, 308, 23, 48, 289, 290; 607/50; 128/640

[56] References Cited

U.S. PATENT DOCUMENTS

| | | |
|---|---|---|
| 4,902,278 | 2/1990 | Maget et al. . |
| 4,921,475 | 5/1990 | Sibalis . |
| 4,969,881 | 11/1990 | Viesturs . |
| 5,080,099 | 1/1992 | Way et al. . |
| 5,336,209 | 8/1994 | Porzilli ..................................... 604/307 |
| 5,338,412 | 8/1994 | Burk et al. . |

OTHER PUBLICATIONS

Topical Hyperbaric Therapy for Problem Skin Wounds, Madalene Cy.Y. Heng, MB, FRACP, 1993 by Elsevier Science Publishing Co., Inc.

Primary Examiner—Scott M. Getzow
Attorney, Agent, or Firm—Fay, Sharpe, Beall, Fagan, Minnich & McKee

[57] ABSTRACT

A portable, self-contained device is described for the topical application of oxygen to promote the healing of skin wounds. The device is comprised of a wound dressing that incorporates an electrochemical, chemical, or thermal means of generating high purity oxygen. The device can regulate the supply of oxygen to an area above the wound at various concentrations, pressures and dosages. The device is driven by a built in or accessory power source. Ambient air is brought into contact with a gas permeable cathode. Oxygen present in the air is reduced at the cathode to negative ions (i.e. peroxide, superoxide or hydroxyl ions) and/or their unprotonated and protonated neutral species. One or more of these species diffuse through an electrolyte and are then oxidized at a gas permeable anode to produce a high concentration of oxygen directly above the wound. Oxygen can also be depleted from that same area by reversing the polarity of the power source allowing the supply of oxygen to the wound to be modulated, thereby controlling the rate of healing.

22 Claims, 1 Drawing Sheet

OXYGEN PRODUCING BANDAGE

This is a continuation of application Ser. No. 08/421,679 filed on Apr. 12, 1995 now U.S. Pat. No. 5,578,022.

BACKGROUND OF THE INVENTION

The present invention is directed to the art of bandages, wound dressings, or patches useful in modulating the supply of oxygen to skin wounds. The invention is particularly useful in supplying localized and predetermined dosages of concentrated oxygen directly to skin wounds topically without incurring systemic toxic side effects associated with extreme amounts of oxygen, as may occur in connection with hyperbaric oxygen chamber techniques of the prior art.

Hyperbaric oxygen therapy is used for inducing the growth of blood vessels for stimulating growth of new skin tissue to close and heal ischemic wounds. The systemic therapy has its drawbacks, however. For example, hyperbaric oxygen may produce vasoconstriction, toxicity and tissue destruction. When offered systemically, there is a risk of central nervous system and pulmonary toxicity. Topical hyperbaric oxygen therapy, on the other hand, avoids systemic toxicity but is useful for open wounds and has proven effective in healing recalcitrant skin wounds. The toxic effect from excessive topical oxygen can lead to cessation of healing as it can be toxic to endothelial cells surrounding the wound. Devasculation occurs, and neovasculation ceases. Any damage caused by a toxic dose of topical oxygen is, however, typically cured in about two weeks by simply stopping the treatment.

Topical hyperbaric oxygen therapy calls for applying oxygen directly to an open wound. The oxygen dissolves in tissue fluids and improves the oxygen content of the intercellular fluids. Such direct application of oxygen to the wound has advantages. For example, because it is applied directly to the base of an ulcer, much lower pressures of oxygen are required for stimulating wound healing as compared to systemic oxygen therapy where diffusion is needed. Skin disorders which may be treated with topical hyperbaric oxygen include osteomyelitis, burns and scalds, necrotizing fasciitis, pyoderma gangrenosum, refractory ulcers, diabetic foot ulcers, and decubitus ulcers (bed sores). Cuts, abrasions and surgically induced wounds or incisions may also benefit from topical oxygen therapy.

The prior art teaches application of topical hyperbaric oxygen by placing the entire affected limb of a person in a sealed chamber such as one which features controlled pressure sealing and automatic regulation control. The chamber provides oxygen at hyperbaric or normobaric pressure to the entire extremity rather than only the wound site. Such hyperbaric oxygen chambers for extremities have drawbacks in that they are expensive, difficult to sterilize and have a potential for cross-infection. A suggestion for overcoming these drawbacks calls for replacing the permanent chamber with a disposable polyethylene bag. While this technique will remove the problems of sterilization, and part of the expense, it still has its disadvantages. For one, an external source of oxygen must be supplied. Even though the chamber may be quite small, pressurized oxygen, even at pressures as low as 1.04 atm, must be supplied from an external reserve. This requires a patient to be positioned near an oxygen tank during treatment. Moreover, because an entire limb is placed in a chamber or polyethylene bag, large areas of skin may be unnecessarily subjected to potentially toxic levels of oxygen. Also, the sealing mechanism of the chamber or bag may cause an undesirable tourniquet effect on the limb that is undergoing treatment.

The present invention contemplates an improved device and method for modulating the supply of concentrated hyperbaric oxygen to skin wounds. The device is disposable and therefore eliminates the risk for cross contamination. Also, it frees a patient from being confined to a pressurized source of oxygen. Hyperbaric oxygen may be supplied directly to localized areas of skin economically and conveniently without unnecessarily restricting blood flow to the treatment area. In addition, this device is capable of depleting the wound site of oxygen, which may lead to cell hypoxia. Moderately severe hypoxia has been found to promote capillary budding and proliferation. New capillaries are formed (neo-angiogenesis) in response to initial tissue hypoxia. As a result of increased blood flow, the increased oxygen tension in the tissues stimulates a complex healing process to close the wound. Thus, by increasing or decreasing (i.e., modulating) oxygen supply, one can stimulate wound healing in a most advantageous manner.

BRIEF DESCRIPTION OF THE INVENTION

The present invention is directed to a device and method for providing a topical treatment of modulated hyperbaric oxygen to skin wounds. The device comprises a wound dressing patch or bandage adapted for receipt over a skin wound treatable with oxygen. The device further incorporates an oxygen regulator or concentrator which generates oxygen according to an electrochemical process and supplies it to a skin wound.

The method of treating wounds by hyperbaric oxygen in accordance with the present invention calls for placing an oxygen generating bandage over a skin wound. Ambient air is brought into contact with a gas permeable cathode incorporated in the bandage. Oxygen present in the air is reduced to negatively charged ions, i.e. superoxide and peroxide and their various unprotonated and protonated neutral states ($HO_2$, $HO_2^-$, $O_2^{2-}$) or hydroxyl ions or undissociated $H_2O_2$ at the cathode according to a one, two or four electron process. One or more of these species then diffuse through an electrolyte, and are oxidized at the anode to produce a high concentration (about 100%) of oxygen. The oxygen passes to the skin wound from the anode. An enriched oxygen environment is sustained under hyperbaric pressure during the treatment cycle.

The electrochemical process is driven by an internal or external power source. Reversing the polarity of the power source reverses the process so that a very low level of oxygen (as low as about 0% oxygen concentration) is supplied to the wound, hence modulating the level of oxygen in the wound treatment area. The modulation of the level of oxygen will control the rate of wound healing by increasing or decreasing the oxygen tension in the tissues that stimulate healing.

An advantage of the present invention is that concentrated oxygen may be supplied topically to a skin wound without running the risk of supplying toxic amounts of the oxygen to the wound or areas surrounding the wound. Toxic effects from systemic administration are avoided.

Another advantage of the present invention is that the bandage or wound dressing itself is portable and generates hyperbaric oxygen from ambient air for supply to a patient without the need for an external supply of pressurized oxygen.

Another advantage is that the bandage has full occlusion around the wound site. The fully enclosed wound is protected from aerobic infection while anaerobic bacteria are destroyed by the oxygen therapy. Further sterilization also occurs inside the bandage both chemically (i.e. via traces of electrogenerated peroxide) as well as electrochemically, by electrochemical destruction at the electrodes.

Yet another advantage of the present invention is that the bandage provides an economical and convenient device for supplying hyperbaric oxygen to skin wounds. The oxygen bandage may be operated at various pressures, for example, in the range of 0.5 to 5 atmospheres, but more preferably in the range of 0.75 to 2.5 atmospheres, and most preferably in the range of 0.95 to 1.1 atmospheres. The actual pressure or pressures of operation will be dependent on such variables as oxygen concentration required, type of wound being healed, duration, patient comfort, etc. For example, pressures which are quite low or quite high could be desirable for shorter durations than intermediate pressures.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment which will be described in detail in this specification and illustrated in the accompanying drawings which form a part hereof.

DETAILED DESCRIPTION OF THE PREFERRED EMBODIMENT

Figure 1:
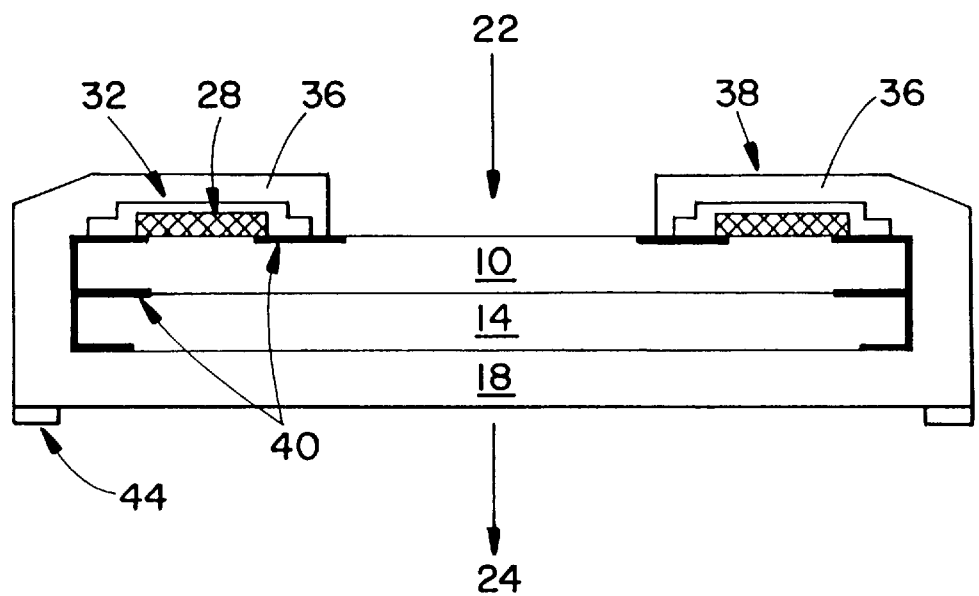
FIG. 1 is a schematic representation of a side view of an oxygen producing patch in accordance with the present invention.

Referring now to the drawings wherein the showings are for purposes of illustrating the preferred embodiment of the invention only and not for purposes of limiting same, the figures show a novel and versatile approach for generating concentrated hyperbaric oxygen to heal skin wounds. Attention is first directed to FIG. 1 which schematically diagrams a side view of the device or patch of the present invention. Dioxygen is produced electrochemically by a three-layer sandwich-type structure comprising a gas-permeable cathode 10, a separator membrane 14 embedded with an immobilized electrolyte, and a gas-permeable anode 18. The cathode is exposed to the atmosphere, and the anode is intended for exposure to a skin wound. The electrolyte may be either alkaline or acidic, such as a proton conducting solid polymer electrolyte film, and either moist or doped with an acid solution.

The device schematically shown in FIG. 1 operates in much the same manner as the device in U.S. Pat. No. 5,338,412, incorporated herein by reference. In that patent, dioxygen supplied from the air is reduced to hydrogen peroxide ions which travel through a thin electrolyte. The ions are oxidized at the anode to supply concentrated oxygen. The patch or bandage described herein supports a much broader spectrum of oxygen concentration processes. Here, dioxygen supplied from the atmospheric air at 22 is reduced at the gas-permeable cathode 10 to negatively charged ions i.e. superoxide and peroxide and their various unprotonated and protonated states ($HO_2$, $HO_2^-$, $O_2^{2-}$) or hydroxyl ions or undissociated $H_2O_2$ according to a one, two or four electron process. The cathode is of the type used in fuel cells. One or more of these species then travel through the thin separator/electrolyte structure or membrane 14 to the gas permeable anode 18, where they are reconverted into dioxygen. The dioxygen flows out of the anode at 24 and is intended to be directed to a skin wound.

The patch shown in FIG. 1 is powered by an air driven battery, in this case a zinc/air battery, with components similar to those used in conventional hearing aid batteries, and built directly onto the three layer structure. It takes advantage of a bipolar-type design to simplify manufacturing. As indicated, a small amount of zinc powder is mixed, as is customary, with a gelled alkaline electrolyte and placed on top of the gas fed cathode as a zinc electrode 28. It is then fully covered with a separator or membrane 32. To complete the battery, the gas fed anode 18 is folded around the structure and placed directly on top of the separator to become the battery cathode 36. In other words, a single gas permeable electrode plays a dual role. It is both the anode 18 for the generation of oxygen at 24, and the cathode 36 or air electrode in the zinc/air battery design. During operation, air flows to the zinc/air battery such as exemplified at 38.

Electrical insulators 40 are positioned around the cathode 10, membrane 14, membrane 32 and cathode 36 as indicated in FIG. 1, to properly isolate both electronically and ionically each of the active components of the bandage and battery. Adhesive is depicted at 44 for affixing the patch over a skin wound such that oxygen cannot flow readily out of the treatment area. The patch will have some one way valves or small capillary holes to permit outflow of air. The bandage is occlusive on all sides and offers anti-bacterial control without antibiotics or antiseptics, although these can still be used for added protection.

The oxygen generating bandage itself may have multiple layers to promote patient comfort and healing, including but not limited to layers of cotton gauze, polyethylene oxide-water polymer, as well as layer(s) containing topical ointments and other medicinals including antibiotics, antiseptics, growth factors and living cells. Additional layers may comprise a battery, a sensor and/or an oxygen concentrator. There is not a prerequisite ordering to the layers, and not all the layers need be included to have a working device.

The device shown in FIG. 1 has several advantages. For example, the amount of zinc can be controlled so as to generate a fixed amount of dioxygen. In this fashion, the possibility of an oxygen overdose (which has been found to have detrimental biological effects that lead to the cessation of healing), such as by the patient's failure to remove the patch after the treatment period, can be completely averted. The air electrodes, and thus the zinc/air battery as a whole, can be sealed during production and activated by exposure of the oxygen cathode 10 to the atmosphere immediately before use.

Figure 2:
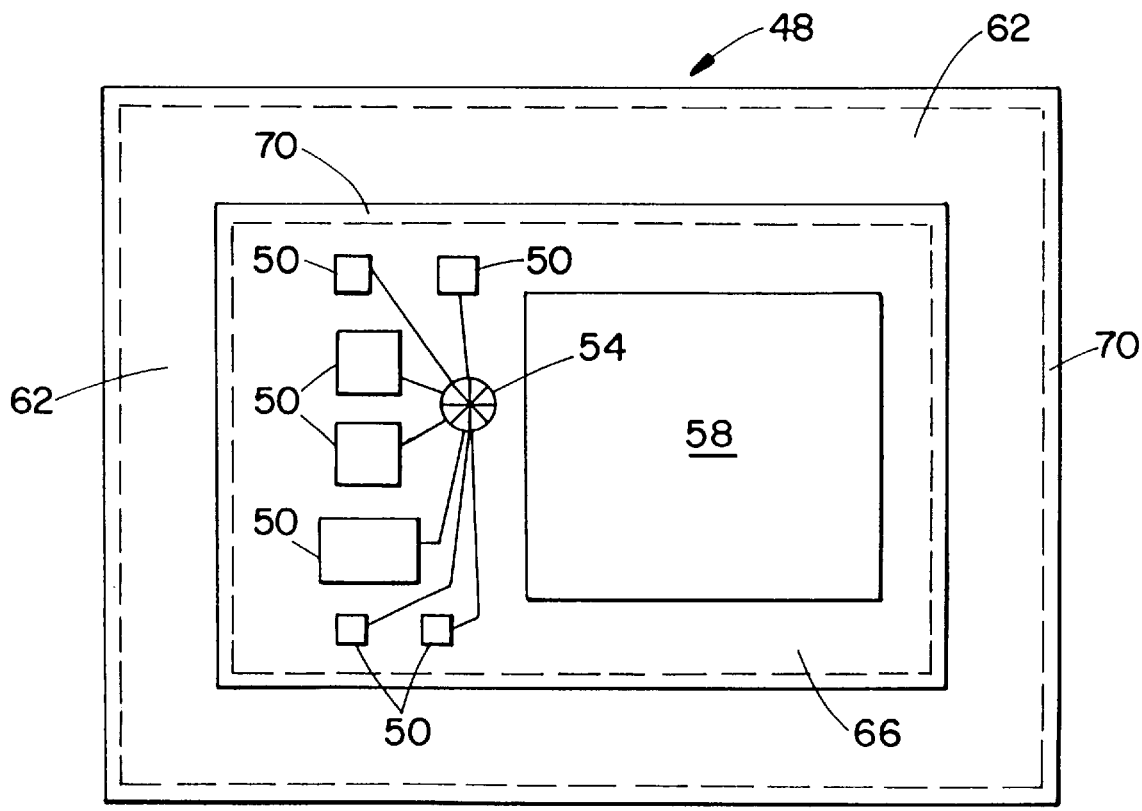
FIG. 2 is a schematic representation of a plan view of an oxygen producing patch incorporating a plurality of batteries in accordance with the present invention.

With attention now directed to FIG. 2, single patch 48 can be equipped with several sealed zinc/air batteries 50. This will enable the patient to apply oxygen intermittently as is usually the case with present treatments. Each battery may be manufactured according to a predetermined life span. For example, each of the batteries can be set to last for 1 hour, 2 hours, 4 hours, more time or less time. Differently sized batteries can be incorporated into a single patch so the same patch can be maintained in place for a period of time before the dressings are removed for cleansing of the wound. This permits differently timed dosages of oxygen to be applied to a wound. For example, a one hour therapy can take place on day 1, followed by a 2 hour therapy on day 2, and so on. Each battery includes a peel off sticker. When the sticker is removed, the zinc/air battery or other air driven battery is exposed to the air and begins operating. The oxygen generating portion is depicted at 54.

In the alternative to having multiple batteries, a single battery having an electronic timing device may be included for a seven day or longer oxygen therapy treatment. Longer treatments are within the scope of the invention; however, it is impractical because the wound dressings must be removed periodically so the wound can be cleansed. Because of its monolithic construction, patches can, in principle, be manufactured in any size or shape, even including a transparent plastic window directly above the wound to visually monitor the healing progress (neovascularization) without having to remove the patch. FIG. 2 shows such a viewing or inspection window at 58. In use, the wound would be located below the window. As shown in FIG. 1, the patch can be affixed to the skin with a simple adhesive layer 44 around the perimeter. The patch may be made in many shapes such as gloves, socks, sleeves, etc. and may be cut to size.

FIG. 2 shows an alternative embodiment which incorporates a plastic frame 62. The frame surrounds the oxygen producing bandage 66. The plastic frame includes an adhesive along its edges 70 for securing the frame to the skin. The oxygen producing bandage is supported by the frame. The adhesive along edges 70 provides a seal against escaping oxygen. The bandage can then be removed without disrupting the skin of the patient. Patient comfort is enhanced. The plastic frame may contain or define openings which serve as one way pressure or relief valves to allow for gas release. Such valves or small capillary holes prevent accidental overpressurization, which could lead to possible bursting of the device. The valves or small capillary holes also serve to eliminate air from the wound cavity during the initial building up of concentrated dioxygen.

In using a patch with the zinc/air battery system shown in FIGS. 1 and 2, it can be shown using Faraday's law that 65.4 grams of zinc produce 22.4 liters of dioxygen at 1 atmosphere of pressure and ambient temperatures.

When the patch is in operation, a small region of the patch has one way valves or is designed with small capillary holes so as to allow gas to flow out of the anode compartment to prevent pressure build up. Ambient air flows through the patch after the treatment is momentarily discontinued to return the wound site to normal ambient air conditions and prevent toxic overexposure to newly formed blood vessels.

The patches shown in FIGS. 1 and 2 portray oxygen producing or modulating bandages. The bandages include built-in electrochemical systems for producing oxygen according to a one, two or four electron process. The reactions are powered by air-driven batteries. The bandages and related electrochemical equipment described in the Figures set forth preferred embodiments of operation.

Oxygen generation and/or depletion may occur according to various electrochemical reactions. In addition to the two electron process already described, the reaction may be based on one or four electrons, or combinations of the one, two and/or four electron processes at all temperatures. As already described, the two electron process involves converting oxygen in the air feed gas to peroxide ions and/or $H_2O_2$ at the cathode, passing the peroxide ions and/or $H_2O_2$ through an electrolyte, and converting the peroxide ions and/or $H_2O_2$ to oxygen at the anode. A one-electron process involves converting the feed oxygen to superoxide ions or its protonated form, passing the superoxide ions or its protonated form through the electrolyte, and converting the superoxide ions or its protonated form to oxygen at the anode. A more energy demanding approach involves reducing oxygen contained in a feed gas and/or generating hydrogen gas ($H_2$) via a four electron process. This involves the electrolysis of water. Here, hydroxyl ions and/or ($H_2$) are generated, and the electrode denoted as 18 in FIG. 1 oxidizes water via a four electron process, to yield dioxygen. Such a strategy calls for catalysts in one or both electrodes to overcome the kinetic irreversibility of the reactions. The amount of hydrogen formed under actual operating conditions would, however, be expected to be very small and thus pose no hazard.

In situations where it is desired to provide concentrated oxygen to a wound site, the anode faces the wound. In creating an oxygen deficient atmosphere within the treatment area, the polarity of the power supply to the patch is reversed so as to reduce oxygen on the electrode in contact with the treatment area. This electrode then acts as the cathode, and oxygen is generated on the electrode in contact with the ambient atmosphere, the anode electrode. Oxygen is supplied to the skin wound at pressures varying below and above atmospheric pressure. When the need arises to reverse polarity, a power supply other than the bipolar built-in battery may be required.

It is fully within the scope of this invention to drive the oxygen modulating (i.e. oxygen producing and/or depleting) reaction according to a variety of methods. Power to the oxygen concentrator may be supplied from other sources separate from the patch. A separate power control mechanism may contain or comprise electronic timing, both primary and secondary batteries, capacitors, supercapacitors, photovoltaic cells, convertors for connection to alternating current (A.C.) power, and bipolar built-in batteries as previously described. These power sources may be positioned within the bandage/patch or externally thereto.

The methods used for generating and depleting oxygen are preferably electrochemical in nature, although nonelectrochemical methods may be practiced to achieve a modulation of the oxygen content in the treatment area. For example, chemically or thermally induced reactions that could release or absorb oxygen in a controlled fashion may be employed. These methods may also include inexpensive sensors and control circuitry for oxygen concentration, humidity, pressure, and other conditions for monitoring and controlling parameters (i.e. current density) and for promoting optimal healing.

The invention has been described with reference to the preferred embodiment. Obviously modifications and alterations will occur to others upon a reading and understanding of this specification. It is intended to include all such modifications and alterations insofar as they come within the scope of the appended claims or the equivalent thereof.

We claim:

1. A device for supplying oxygen to skin, comprising:
   an oxygen-generating covering adapted for receipt over skin; and
   an oxygen generating device incorporated within the covering for generating oxygen and supplying the generated oxygen to the skin.

2. A device for supplying oxygen to skin, according to claim 1, wherein the supply of oxygen may be modulated between 0% and 100% oxygen concentration.

3. A device for supplying oxygen to skin, according to claim 1, wherein the oxygen generating device generates oxygen electrochemically and includes:
   a cathode for reducing oxygen in a feed gas to negative ions and/or neutral species;
   an electrolyte for diffusing the negative ions and/or neutral species therethrough; and
   an anode communicating with the electrolyte for oxidizing the negative ions and/or neutral species to produce a high concentration of oxygen for supply to the skin.

4. A device for supplying oxygen to skin, according to claim 3, wherein the production of oxygen occurs according to a one, two or four electron process.

5. A device for supplying oxygen to skin, according to claim 3, wherein the negative ions are peroxide ions in their various unprotonated and protonated forms.

6. A device for supplying oxygen to skin, according to claim 3, wherein the negative ions are superoxide ions including their protonated form.

7. A device for supplying oxygen to skin, according to claim 3, wherein the negative ions are hydroxyl ions and the overall process involves electrolysis of water.

8. A device for supplying oxygen to skin, according to claim 1, wherein the oxygen generating device generates oxygen according to an electrochemical process and includes a power source which applies a potential difference between a cathode and anode to generate concentrated oxygen from ambient air.

9. A device for supplying oxygen to skin, according to claim 8, wherein the power source is incorporated into the device.

10. A device for supplying oxygen to skin, according to claim 9, wherein the power source is a bipolar battery incorporated into the device.

11. A device for supplying oxygen to skin, according to claim 9, wherein a zinc/air battery incorporated into the device supplies power to conduct the concentration of oxygen from air according to a one, two or four electron process.

12. A device for supplying oxygen to skin, according to claim 8, wherein the power source is external to the device.

13. A device for supplying oxygen to skin, according to claim 8, wherein the power source is selected from the group consisting of capacitors, supercapacitors, photovoltaic cells, batteries, and alternating current power.

14. A device for supplying oxygen to skin, according to claim 8, wherein polarity on the power source is reversible to modulate the oxygen concentration.

15. A device for supplying oxygen to skin, according to claim 1, wherein the oxygen regulating device generates oxygen according to a thermally induced reaction.

16. A device for supplying oxygen to skin, according to claim 1, wherein the oxygen regulating device generates oxygen according to a chemically induced reaction.

17. A device for supplying oxygen to skin, according to claim 1, wherein the oxygen regulating device modulates a supply of oxygen to the skin at various pressures ranging from below atmospheric pressure to above atmospheric pressure.

18. A device for supplying oxygen to skin, according to claim 17, wherein the pressures range from about 0.5 atmospheres to about 5 atmospheres.

19. A device for supplying oxygen to skin, according to claim 17, wherein the pressures range from about 0.75 atmospheres to about 2.5 atmospheres.

20. A device for supplying oxygen to skin, according to claim 17, wherein the pressures range from about 0.95 to about 1.1 atmospheres.

21. An oxygen supplying device, comprising:
an oxygen-producing sheath incorporating as part of said sheath an electrochemical oxygen concentrator including a cathode for reducing oxygen in a feed gas such as ambient air to negative ions and/or neutral species, an electrolyte for diffusing the negative ions and/or neutral species therethrough, and an anode communicating with the electrolyte for oxidizing the negative ions and/or neutral species to produce a high concentration of oxygen.

22. An oxygen producing covering, comprising:
a covering containing an oxygen concentrating device for concentrating oxygen according to an electrochemical process, said device including a power source which applies a potential difference between a cathode and anode to generate concentrated oxygen from ambient air.

* * * * *